(12) United States Patent
Woolston

(10) Patent No.: US 9,636,276 B2
(45) Date of Patent: May 2, 2017

(54) MEDICAMENT CARTRIDGE ASSEMBLY

(71) Applicant: DCA DESIGN INTERNATIONAL LIMITED, Warwick (GB)

(72) Inventor: Robert Woolston, Warwick (GB)

(73) Assignee: SANOFI-AVENTIS DEUTSCHLAND GMBH, Frankfurt (DE)

( * ) Notice: Subject to any disclaimer, the term of this patent is extended or adjusted under 35 U.S.C. 154(b) by 0 days.

(21) Appl. No.: 14/587,275

(22) Filed: Dec. 31, 2014

(65) Prior Publication Data

US 2015/0119811 A1    Apr. 30, 2015

Related U.S. Application Data

(63) Continuation of application No. 13/756,200, filed on Jan. 31, 2013, now abandoned, which is a
(Continued)

(30) Foreign Application Priority Data

Dec. 6, 2001    (GB) .................................. 0129176.4

(51) Int. Cl.
  *A61J 1/00*      (2006.01)
  *A61J 1/18*      (2006.01)
(Continued)

(52) U.S. Cl.
  CPC ................. *A61J 1/18* (2013.01); *A61J 1/062* (2013.01); *A61M 5/24* (2013.01); *A61J 1/1418* (2015.05);
(Continued)

(58) Field of Classification Search
  CPC .... A61J 1/10; A61J 1/1406; A61J 1/18; A61J 1/062; A61J 1/1418; A61J 2205/20;
(Continued)

(56) References Cited

U.S. PATENT DOCUMENTS 2,254,559 A * 9/1941 Heyerdahl .................... 220/784
2,834,346 A * 5/1958 Adams .......................... 604/242
(Continued)

FOREIGN PATENT DOCUMENTS

EP    0 063 891 A1    11/1982
EP    0 550 767 A1    7/1993
(Continued)

OTHER PUBLICATIONS

Feb. 18, 2011 Office Action issued in U.S. Appl. No. 12/461,951.
(Continued)

*Primary Examiner* — James N Smalley
(74) *Attorney, Agent, or Firm* — Oliff PLC

(57) ABSTRACT

An adaptor top for a medicament cartridge, the medicament cartridge including a cylinder having a main body portion, a neck portion at a first end having a radially outwardly directed flange portion, a narrowing shoulder portion connecting the body portion and the neck portion, a cap beaded across the first end thereby to retain a fluid impermeable membrane, and the adaptor top comprising a first cylindrical body portion having a radially inwardly directed flange at one end, in use to be seated over and against the cap and a second cylindrical skirt portion being adapted, in use, to be seated against the shoulder portion of the cartridge, the second skirt portion including a plurality of fingers, the free ends of the fingers in use being adapted to be seated beneath the outwardly directed flange of the medicament cartridge.

9 Claims, 1 Drawing Sheet

Related U.S. Application Data continuation of application No. 12/461,951, filed on Aug. 28, 2009, now Pat. No. 8,387,809, which is a continuation of application No. 11/438,275, filed on May 23, 2006, now abandoned, which is a continuation of application No. 10/308,148, filed on Dec. 3, 2002, now abandoned.

(51) Int. Cl.
| | | |
|---|---|---|
| *A61J 1/06* | (2006.01) | |
| *A61M 5/24* | (2006.01) | |
| *A61M 39/10* | (2006.01) | |
| *A61J 1/14* | (2006.01) | |

(52) U.S. Cl.
CPC ........... *A61J 2205/20* (2013.01); *A61M 39/10* (2013.01); *A61M 2039/1038* (2013.01); *A61M 2205/6081* (2013.01); *Y10T 29/49826* (2015.01)

(58) Field of Classification Search
CPC .................. B65D 51/002; A61M 5/24; A61M 2039/1038; A61M 39/10; A61M 2205/6081; Y10T 29/49826
USPC ................... 215/317, 247, 249, 230, DIG. 3; 604/411, 415
See application file for complete search history.

(56) References Cited

U.S. PATENT DOCUMENTS

| | | | |
|---|---|---|---|
| 3,375,825 A | 4/1968 | Keller | |
| 3,395,642 A * | 8/1968 | Foster et al. .................. | 102/317 |
| 3,916,893 A | 11/1975 | De Felice | |
| 3,977,555 A | 8/1976 | Larson | |
| 4,018,640 A | 4/1977 | Amberg | |
| 4,211,333 A * | 7/1980 | Villarejos ..................... | 215/249 |
| 4,402,417 A | 9/1983 | Corrigan, Jr. et al. | |
| 5,085,332 A | 2/1992 | Gettig et al. | |
| 5,088,996 A | 2/1992 | Kopfer et al. | |
| 5,137,528 A | 8/1992 | Crose | |
| 5,230,707 A | 7/1993 | Laderoute | |
| 5,303,835 A | 4/1994 | Haber et al. | |
| 5,334,162 A | 8/1994 | Harris | |
| 5,344,417 A | 9/1994 | Wadsworth, Jr. | |
| 5,360,410 A | 11/1994 | Wacks | |
| 5,454,409 A | 10/1995 | McAffer et al. | |
| 5,468,232 A | 11/1995 | Naganuma | |
| 5,549,561 A | 8/1996 | Hjertman | |
| 5,641,010 A | 6/1997 | Maier | |
| 5,688,250 A | 11/1997 | Naganuma | |
| 5,693,027 A | 12/1997 | Hansen et al. | |
| 5,709,668 A | 1/1998 | Wacks | |
| 5,819,964 A * | 10/1998 | Grimard ....................... | 215/249 |
| 5,957,314 A | 9/1999 | Nishida et al. | |
| 5,971,181 A | 10/1999 | Niedospial, Jr. et al. | |
| 5,971,183 A | 10/1999 | Bartsch | |
| 6,126,646 A | 10/2000 | Hansen et al. | |
| 6,227,371 B1 | 5/2001 | Song | |
| 6,328,174 B1 | 12/2001 | Marangoni Graziani et al. | |
| 6,379,340 B1 | 4/2002 | Zinger et al. | |
| 6,745,505 B2 | 6/2004 | Moran | |
| 6,904,867 B2 | 6/2005 | Zamjahn | |

FOREIGN PATENT DOCUMENTS

| | | |
|---|---|---|
| EP | 0 829 248 A2 | 3/1998 |
| EP | 0 937 473 A2 | 8/1999 |
| EP | 0 990 446 A1 | 4/2000 |
| EP | 1 094 012 A2 | 4/2001 |
| GB | 2 190 303 A | 11/1987 |
| JP | 11-500986 A | 1/1999 |
| WO | 80/00828 A1 | 5/1980 |
| WO | 89/07462 A1 | 8/1989 |
| WO | 92/04926 A1 | 4/1992 |
| WO | 93/02720 A1 | 2/1993 |
| WO | 93/02725 A1 | 2/1993 |
| WO | 97/22526 A2 | 6/1997 |
| WO | 2005/049443 A1 | 6/2005 |

OTHER PUBLICATIONS

Jul. 27, 2011 Office Action issued in U.S. Appl. No. 12/461,951.
Mar. 15, 2012 Office Action issued in U.S. Appl. No. 12/461,951.
Aug. 10, 2012 Final Office Action issued in U.S. Appl. No. 12/461,951.
Oct. 30, 2012 Notice of Allowance issued in U.S. Appl. No. 12/461,951.
Oct. 1, 2014 Office Action issued in U.S. Appl. No. 13/756,200.
Mar. 12, 2014 Office Action issued in U.S. Appl. No. 13/756,200.
Aug. 22, 2013 Office Action issued in U.S. Appl. No. 13/756,200.
May 24, 2013 Office Action issued in U.S. Appl. No. 13/756,200.

* cited by examiner

MEDICAMENT CARTRIDGE ASSEMBLY

This is a Continuation of application Ser. No. 13/756,200 filed Jan. 31, 2013, which is a Continuation of application Ser. No. 12/461,951 filed Aug. 28, 2009, which is a Continuation of application Ser. No. 11/438,275 filed May 23, 2006, which is a Continuation of application Ser. No. 10/308,148 filed Dec. 3, 2002. The disclosures of these prior applications are hereby incorporated by reference herein in their entirety.

FIELD OF THE INVENTION

The present invention relates to an improved medicament cartridge assembly and, in particular, but not exclusively, to a medicament cartridge assembly for use with a medication delivery apparatus such as an injection pen or an infuser.

Such medication delivery apparatus are conveniently used to provide a means for administration of a medicament to a patient without medical supervision, for example, by self administration or administration by a carer.

BACKGROUND TO THE INVENTION

Medicament cartridges are produced in large volumes to take advantage of economies of scale. The medicament cartridges will then be filled with an appropriate medicament, such as insulin or a human growth hormone.

However, it is often the case that a patient will require more than one form of medicament. A person having diabetes will often be required to take both slow acting and fast acting forms of insulin. It is important that a user of the medicament delivery apparatus is able to distinguish readily between medicament cartridges containing different medicaments.

It is an advantage of the present invention that it enables the user to distinguish readily between medicament cartridges containing different medicaments. It is a further advantage that the present invention makes use of known medicament cartridges, thereby enabling economies of scale to be maintained.

SUMMARY OF THE INVENTION

According to the first aspect of the present invention there is provided an adaptor top for a medicament cartridge, the medicament cartridge comprising a cylinder having a main body portion, a neck portion at a first end having a radially outwardly directed flange portion, a narrowing shoulder portion connecting the body portion and the neck portion, a cap beaded across the first end thereby to retain a fluid impermeable membrane, the adaptor top comprising a first cylindrical body portion having a radially inwardly directed flange at one end, in use to be seated over and against the cap and a second cylindrical skirt portion being adapted, in use, to be seated against the shoulder portion of the cartridge, the second skirt portion including a plurality of fingers, the free ends of the fingers in use being adapted to be seated beneath the outwardly directed flange of the medicament cartridge.

According to a second aspect of the present invention, a method of assembling a medicament cartridge and an adaptor top, the medicament cartridge comprising a cylinder having a bottleneck at a first end, a fluid impermeable membrane secured across the first end by a cap and a displaceable plunger located internally of the cylinder towards the second end of the cylinder, and the adaptor top comprising a first cylindrical portion having at a first end an inwardly directing flange and a second cylindrical portion depending from a second end of the first cylindrical portion, the second cylindrical skirt portion including a number of deformable members, comprising the steps of inserting the cap of the medicament cartridge through the second cylindrical portion into the first cylindrical portion until the cap is positioned against the inwardly directed flange;

plastically deforming the deformable members beneath the cap to retain the adaptor top in position against the medicament cartridge.

The adaptor top may conveniently be provided with information regarding the content of the medicament cartridge. Preferably, the adaptor top is colour coded to provide information regarding the content of the medicament cartridge.

BRIEF DESCRIPTION OF THE DRAWINGS

The present invention will now be described, by way of example only, with reference to the accompanying drawings, in which.

DETAILED DESCRIPTION OF THE INVENTION

Figure 1:
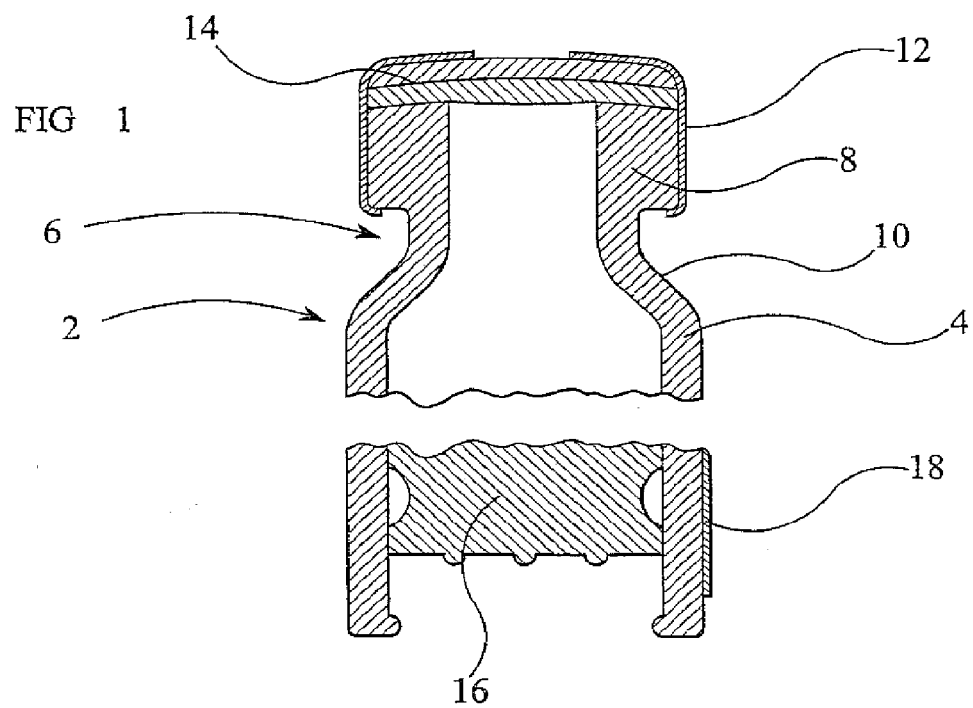
FIG. 1 shows a part-cut-away section through a known medicament cartridge.

Referring to FIG. 1 there may be seen a known cartridge for use with the present invention. The medicament cartridge 2 comprises a cylinder 4 having a main body portion. A neck portion 6 is provided at first end of the body portion. The neck portion 6 includes a radially outwardly directed flange portion 8. A narrowing shoulder portion 10 connects the body portion and the neck portion 6. A cap 12 is provided beaded across the first end of the cylinder 4 thereby to retain a fluid impermeable membrane 14 across an open end of the neck portion 6.

A piston 16 is provided within the cylinder 4. In use, a needle unit (not shown) pierces the fluid impermeable membrane 14 such that movement of the piston 16 towards the first end of the body portion causes the contents of the medicament cartridge to be expelled through the needle unit. The cylinder 4 may additionally be provided with a label 18 providing information about the medicament cartridge 2 and the contents of the medicament cartridge 2.

Figure 2:
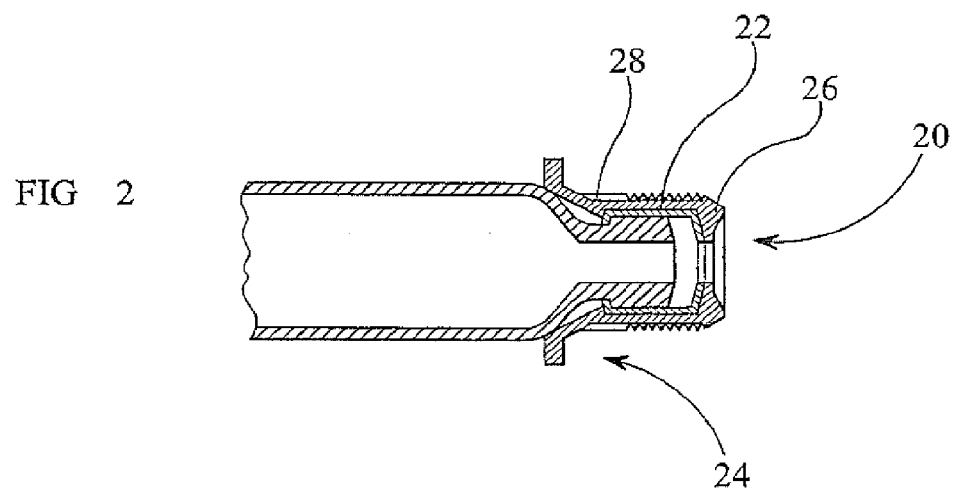
FIG. 2 shows a section through a medicament cartridge assembly in accordance with the present invention.
Figure 3:
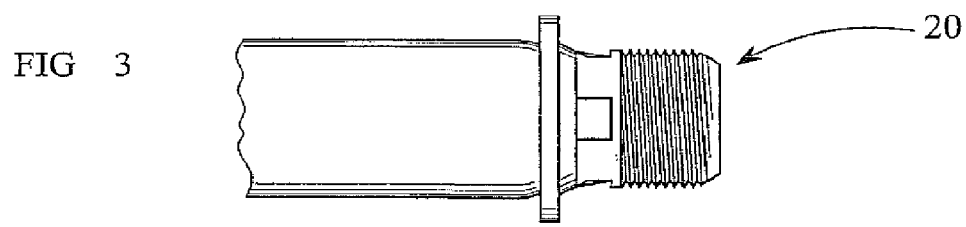
FIG. 3 shows a side view of the assembly of FIG. 2.

Referring now to FIGS. 2 and 3 an adaptor top 20 for a medicament cartridge is shown. The adaptor top 20 comprises a first cylindrical body portion 22 and a second skirt portion 24. The first cylindrical body portion 22 has a radially inwardly directed flange 26 at one end. In use the radially inwardly directed flange is seated over and against the cap 12 and the second skirt portion 24 is seated against the shoulder portion 10 of the cartridge 2.

The first cylindrical body portion 22 is conveniently formed with engagement means. In the embodiment of FIG. 3 the engagement means takes the form of a screw thread 23 formed integrally with the first cylindrical body portion 22. In use, the engagement means enables an assembly comprising the medicament cartridge 2 and adaptor top 20 to be received and secured within a medicament delivery apparatus such as an infusion or injection device from which the contents of the medicament cartridge 2 may be dispensed.

The second skirt portion 24 includes a plurality of deformable members or fingers 28. The fingers 28 are formed at a first end integrally with the adaptor top 20. The fingers 28 are plastically deformable.

In order to assemble the adaptor top 20 with the medicament cartridge 2, the cap 12 of the medicament cartridge 2 is inserted through the second skirt portion 24 into the first cylindrical portion 22 until the cap 12 is in contact with the inwardly directed flange 26. The fingers 28 are then plastically deformed such that free ends of the fingers 28 are located beneath the cap 12 thereby to retain the adaptor top 20 in position in relation to the medicament cartridge 2. Since the free ends of the fingers 28 are now located beneath the cap 12 between the cap 12 and the shoulder portion 10 of the cartridge 2, it is difficult for a user or other third party to remove the adaptor top 20 from the medicament cartridge 2 without damaging the fingers 28. In this way, the adaptor top 20 and the associated medicament cartridge 2 provide a tamper evident assembly.

What is claimed is:

1. A medicament cartridge assembly comprising an adaptor top and a medicament cartridge,
    the medicament cartridge comprising a cylinder having a main body portion, a neck portion at a first end having a radially outwardly directed flange portion, a narrowing shoulder portion connecting the body portion and the neck portion, a cap beaded across the first end thereby to retain a fluid impermeable membrane,
    the adaptor top comprising a first cylindrical body portion having a radially inwardly directed flange at one end being seated over and against the cap, and a second skirt portion being seated against the shoulder portion of the cartridge,
    the second skirt portion including a plurality of fingers, free ends of the fingers being seated beneath the outwardly directed flange of the medicament cartridge and being plastically deformed to prevent a removal of the adaptor top from the medicament cartridge without damaging the fingers,
    the second skirt portion having an outer side face being inclined relative to a longitudinal axis of the cartridge and having at one end a radially outwardly directed flange seated against the shoulder portion of the cartridge, an outer face of the flange is substantially normal to the longitudinal axis of the cartridge, the outer side face is between the plurality of fingers and the flange and the outer side face is inclined outwardly toward the flange,
    the adaptor top further comprising a screw thread that enables the medicament cartridge assembly to be received and secured within a medicament delivery apparatus, the screw thread being formed integrally with the first cylindrical body portion, and the screw thread being located between the radially inwardly directed flange and the radially outwardly directed flange portion, and
    when the medicament cartridge assembly is received and secured within the medicament delivery apparatus and when a needle unit pierces the fluid impermeable membrane, a dispense of contents of the medicament cartridge is enabled.

2. The medicament cartridge assembly according to claim 1, in which the adaptor top is provided with information regarding the contents of the medicament cartridge.

3. The medicament cartridge assembly according to claim 1, in which the adaptor top is color coded to provide information regarding the contents of the medicament cartridge.

4. The medicament cartridge assembly according to claim 1, in which the cylinder comprises a displaceable piston.

5. A medicament delivery assembly comprising a medicament delivery apparatus and the medicament cartridge assembly of claim 1, wherein the medicament cartridge assembly is configured to be received in the medicament delivery apparatus.

6. The medicament delivery assembly according to claim 5, in which the cylinder comprises a displaceable piston.

7. The medicament delivery assembly according to claim 5, comprising the needle unit for piercing the fluid impermeable membrane such that movement of the piston towards the first end of the body portion causes the contents of the medicament cartridge to be expelled through the needle unit.

8. The medicament delivery assembly according to claim 5, in which the medicament delivery apparatus is an injection pen.

9. The medicament delivery assembly according to claim 5, in which the medicament delivery apparatus is an infusion pen.

* * * * *